United States Patent [19]

Ashina et al.

[11] Patent Number: 5,068,442
[45] Date of Patent: Nov. 26, 1991

[54] METHOD FOR MAINTAINING THE ACTIVITY OF ZEOLITE CATALYSTS

[75] Inventors: Yoshiro Ashina; Takeyuki Fujita; Kiyonobu Niwa; Takeshi Inagaki; Yuko Nikaido, all of Yokohama, Japan

[73] Assignee: Nitto Kagaku Kogyo Kabushiki Kaisha, Tokyo, Japan

[21] Appl. No.: 353,446

[22] Filed: May 17, 1989

[30] Foreign Application Priority Data

May 20, 1988 [JP] Japan ................. 63-121966

[51] Int. Cl.$^5$ ................. C07C 45/00
[52] U.S. Cl. ................. 564/479; 564/474
[58] Field of Search ............ 564/479, 474, 473

[56] References Cited

U.S. PATENT DOCUMENTS

| 4,370,503 | 1/1983 | Brake | 564/479 |
| 4,418,214 | 11/1983 | Tarcotte | 564/479 |
| 4,582,936 | 4/1986 | Ashina et al. | 564/479 |

Primary Examiner—C. Warren Ivy
Assistant Examiner—Raymond Covington
Attorney, Agent, or Firm—Koda and Androlia

[57] ABSTRACT

There is provided a method for maintaining the activity of a zeolite catalyst in the catalytic production of methylamines from methanol and ammonia using a zeolite catalyst as at least one of catalysts applied, which comprises controlling the amount of aldehyde compounds as impurities flowing into a zeolite catalyst layer to about 0.15 g/hr.kg-cat. or lower, as calculated in terms of formaldehyde.

6 Claims, 2 Drawing Sheets

METHOD FOR MAINTAINING THE ACTIVITY OF ZEOLITE CATALYSTS

BACKGROUND OF THE INVENTION

1. Field of the Art

This invention relates to a method for maintaining the activity of zeolite catalysts in the process for producing methylamines from methanol and ammonia with the use of such catalysts. More particularly, this invention relates to a method for maintaining the activity of zeolite catalysts by suppressing contamination of the reaction system with impurities of a specific kind, which is unavoidable under ordinary conditions.

2. Background Art

In general, methylamines are prepared from methanol and ammonia under the conditions of a pressure of 5 to 40 atm and a reaction temperature of 350° to 450° C., using a solid acid catalyst such as silica-alumina. Three types of methylamines, i.e., mono-, di- and tri-methylamine (hereinafter abbreviated as MMA, DMA and TMA) are formed depending upon the number of methyl groups bonded to the nitrogen atom of ammonia. Such methylamines are all useful as intermediates for various solvents, pharmaceuticals, organic synthesis, dyeing aids, surfactants and so on. However, demand for DMA for use primarily as the starting material of dimethylformamide in large quantities is much greater, say, about ten times the demand for MMA and TMA in Japan. In the presence of such solid acid catalyst, however, the composition of the product is thermodynamically determined and nearly equal amounts of MMA, DMA and TMA are formed at the same time under ordinary conditions. Hence, large proportions of the formed MMA and TMA are returned to the reaction system after separation and reused as the starting materials. Furthermore, in view of equilibrium, there is a need for using a largely excessive amount of ammonia for the purpose of promoting the formation of DMA. Separation and recycling of such excessive methylamines and unreacted ammonia cause the installation to increase in size and the process to consume a large quantity of energy. For the details of such a process, see for example, "Hydrocarbon Processing", 1981, November 1985.

Besides the so-called "conventional catalytic process" as described above in which the reaction involved is governed by thermodynamic equilibrium, there has been recently developed a process for obtaining an unequilibratory reaction product containing predominantly primary or secondary amine (MMA or DMA) by making use of the shape selectivity of zeolite catalysts. In this process, a zeolite (crystalline alumino silicate) having a pore opening diameter of a size intermediate between the critical molecular sizes of primary or secondary amine and tertiary amine is used as a catalyst and the molecules of tertiary amine are prevented from diffusing out of the pores, whereby primary or secondary amine is obtained selectively. With this process, DMA may be selectively produced independently of thermodynamic equilibrium, providing various merits such as considerable decrease in the amounts of MMA and TMA to be recycled and excessive ammonia, reduction in process scale, and energy saving. Specific processes proposed thus far utilizing such zeolite catalysts include a process for predominantly obtaining MMA with the use of ZSM-5 or ZSM-21 (U.S. Pat. No. 4,082,805), a process for predominantly obtaining MMA with the use of mordenite, ferrierite, erionite or clinoputilolite (Japanese Patent Laid-Open Publication No. 56-113747) and a process for predominantly obtaining MMA with the use of levynite (EP107457). Specific processes proposed for predominantly obtaining DMA include those using low-binder A zeolite (Japanese Patent Laid-Open Publication No. 58-69846), Fu-1 (Japanese Patent Laid-Open Publication No. 54-148708), mordenite (Japanese Patent Laid-Open Publication No. 58-49340), mordenite or clinoputilolite (Japanese Patent Laid-Open Publication Nos. 57-4169444 and 59-21005) and Rho, ZK-5, chabasite or erionite (Japanese Patent Laid-Open Publication No. 61-254256).

Although only a few reports are available on the process for the production of methylamines using catalysts giving such unequilibratory compositions, its general aspect is described in Fujita et al, "Catalysts", vol. 129, No. 4 (1987). In such a process, the selectivity for DMA is improved by about twice in comparison with that of the conventional process, i.e., the thermodynamic equilibrium process, whereas the selectivity for TMA is reduced to about 1/5. However, since the zeolite catalyst used has an extremely limited selectivity for TMA and TMA returned to the reaction system shows no substantial reactivity over this catalyst, the productivity of TMA (relative to DMA) is limited to a very narrow range in the presence of such catalyst. In order to solve this problem and with a view to making it possible to produce each methylamine at a wider range of given ratios, it has been proposed to use the conventional equilibrium-governed type of catalyst (non-zeolitic catalyst) together with a zeolite catalyst in parallel or series (Japanese Patent Laid-Open Publication No. 57-169445).

One of the characteristic features of processes for producing methylamines using zeolite catalysts is that the reaction is carried out at a temperature lower than that applied in the prior art. This is because the effect of molecular shape selectivity increases at a low temperature, and the amount of the by-product coke formed decreases with a decrease in the reaction temperature, thus leading to an increase in the service life of the catalyst. Another feature is that methanol is not rendered to be reacted completely, unlike the conventional processes, with the conversion of methanol being usually limited to 80 to 98%. This is because the effect of molecular shape selectivity drops drastically at a conversion exceeding 98%. In most cases, therefore, the unreacted methanol is separated, recovered and recycled to the reaction system for reuse.

In general, coke is formed over a zeolite catalyst in a relatively large amount and tends to have a sharp influence on the catalytic activity of zeolite. In particular, it has been found that a zeolite having an one-dimensional pore structure such as mordenite is apt to be deactivated by coke. In the commercial production of methylamine with the use of a zeolite catalyst, the service life of the catalyst is in general shorter than about two or three months even when a critical low temperature of 300° C. or lower is applied to restraint the formation of coke. This makes the efficient use of zeolite catalysts extremely difficult.

Until now, various methods have been proposed with a view to controlling the amount of coke formed over zeolite catalysts or reduce its influence. For instance, studies have been made on methods relying upon the introduction of a third substance such as Pd or P [Ono, "KAGAKU TO KOGYO (Chemistry and Industry)", 38, 100 (1985)], the control of the acidic nature (acid strength distribution) of catalysts [Sawa et al, the 58th Forum on Catalysts, Proceedings (A)], the selective poisoning of the outer surface activity of catalysts [Dejaifve et al., J. Catal. 70, 123 (1981)], the adjustment of the size of zeolite crystals [Sugimoto et al., "Shokubai (Catalysts)", Vol. 25, 13p (1983)] and the adjustment of the hydrophilic and hydrophobic nature of catalysts [Okazaki et al., "Shokubai", Vol. 25, 4p (1983)]. However, these methods fail to provide an essential solution to the problem of the deactivation of zeolite catalysts by coke. In-practice, a catalyst-regenerating arrangement is required to be incorporated in the processes using zeolite catalysts so as to continuously or frequently regenerate the zeolite catalysts. In the process for the production of methylamines in which the amount of gases passing through a reaction tower is considerably large relative to the output for the aforesaid reasons, however, such regular and frequent regeneration of the catalysts are disadvantageous in view of production costs and productivity. It is thus required that plants be continuously operated over an extended period without any regeneration of catalysts.

SUMMARY OF THE INVENTION

The problems to be solved by the present invention are based on the short service life of zeolite catalysts in a process for the production of methylamines using such catalysts. An object of the present invention is to provide a method which can increase the service life of zeolite catalysts in the process and avoid the regeneration of zeolite catalysts or reduce the cycle of regeneration in the course of operation.

As a result of intensive and extensive studies on the above problems by the present inventors, it has been found that in a process for the production of methylamines with the use of a zeolite catalyst, aldehyde compounds among a number of by-product carbon compounds, especially formaldehyde, are very significantly concerned in the formation of coke, and the service life of zeolite catalyst can be considerably prolonged by controlling the amount of such compounds flowing into a catalyst layer up to a specific value.

According to the present invention, therefore, there is provided a method for maintaining the activity of a zeolite catalyst in the catalytic production of methylamines from methanol and ammonia using a zeolite catalyst as at least one of the catalysts applied, which comprises controlling the amount of aldehyde compounds as impurities flowing into a zeolite catalyst layer to about 0.15 g/hr.kg-cat. or lower, as calculated in terms of formaldehyde.

DETAILED DESCRIPTION OF THE INVENTION

Figure 1:
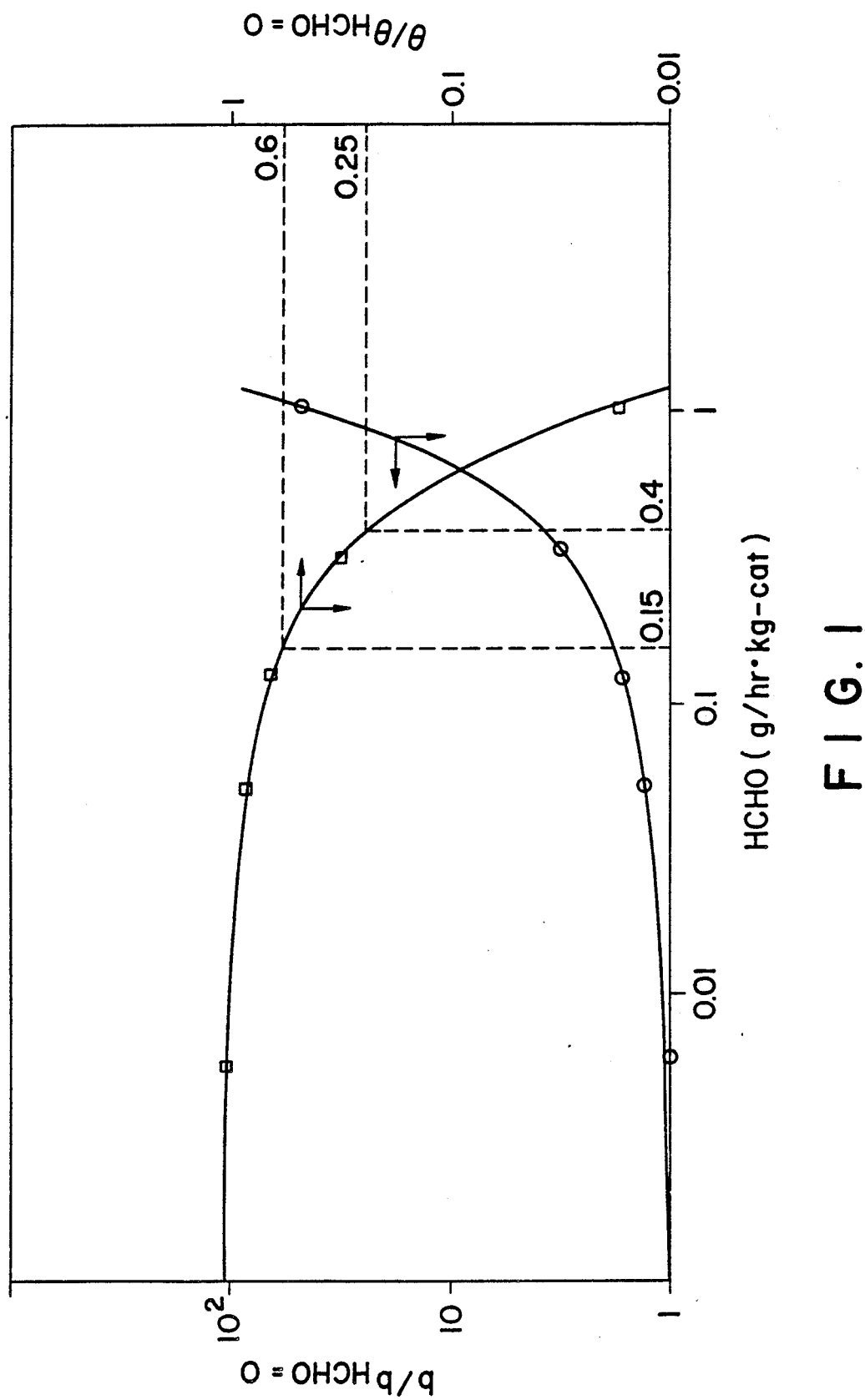
FIG. 1 is a graphical representation of the relation of the deactivation constant and activity half-life (the period in which the rate constant of a methanol-consuming reaction decreases to half) to the amount of formaldehyde that flow into a reactor, wherein the amount of formaldehyde is indicated as abscissa and the deactivation constant $b/b_{HCHO=0}$ (left), which assumes 1 when the amount of formaldehyde is zero, and the activity half-life $\theta/\theta_{HCHO=0}$ (right) as ordinate.

In the production of methylamines, a small amount of compounds such as lower hydrocarbons, e.g. methane or ethane, hydrogen, carbon monoxide, carbon dioxide, dimethyl ether, aldehydes, especially formaldehyde, higher amines and aromatic hydrocarbons, e.g. BTX, are formed as by-products. In the presence of a zeolite catalyst, the amounts of such impurities produced are limited to about ½ to 1/10 in comparison with those obtained in the presence of the conventional amorphous solid acid catalysts, presumably due to its shape selectivity and a lowering of the reaction temperature applied.

In general, the contamination of reaction systems with carbon compounds, whatever they are, is expected to have an adverse influence upon the service life of catalysts, since they provide materials for carbon-forming reactions. According to studies made by the present inventors, it has been found that the influence of carbon compounds other than aldehyde compounds, which may possibly contaminate the reaction system in the process for the production of methylamines, upon the service life of catalysts is much smaller than that of aldehyde compounds, and that aldehyde compounds, especially, formaldehyde, on the other hand, greatly promote the formation of carbon in such trace amounts that other carbon compounds have no influence at all and so give an extremely significant influence upon the service life of catalysts. It is noted that the quantity of such aldehyde compounds present at the reactor inlet is normally as small as less than a few percent of the total impurities flowing into the reactor.

Formaldehyde which contaminates a catalyst layer is primarily formed as by-products in the synthesis reaction of methylamines. Formaldehyde or its compounds are contained in a gaseous reaction product in an amount of about 200 to 300 ppm or higher at a reaction temperature of about 300° C. in the presence of a zeolite catalyst such as mordenite. As it is not possible to separate and remove them under normal purification conditions, nearly entire portion of such aldehyde compounds remain in the recovered methanol stream. In the commercial methylamine production process using a zeolite catalyst, the amount of the formaldehyde compounds entrained per 1 kg of catalyst an hour reaches at about 0.4 g/hr.kg-cat. or higher, as calculated in terms of HCHO. Usually, no problem arises in connection with the actual purity of the starting ammonia and methanol, provided that they are generally of industrial grade. However, it is likely that formaldehyde may contaminate the reaction system, since not only are some generous standards imposed on acetyl compounds but any standards are not placed on formaldehyde. In most cases, the methanol recovered from an identical plant or a different plant offers a good chance of contamination with aldehyde compounds. For instance, the methanol, recovered from a dimethylformamide production plant usually located adjacent to a methylamine production plant contains a lot of aldehyde compounds, and so should be freed of such aldehyde compounds for use as the raw material for methylamines. In order to make it possible to produce the methylamines at a wide range of production ratios, a reactor heretofore available with the conventional equilibrium type of catalyst is often used in combination with a reactor for zeolite catalyst. In this case, the conventional catalyst (amorphous solid acid catalyst) is generally found to give formaldehyde in a larger amount in comparison with the zeolite catalyst (at a reaction temperature of 400° C., it yields formaldehyde more than 10 times as much as the zeolite catalyst at 300° C.). It is thus likely that the reaction system may be contaminated with aldehyde compounds contained in the effluent leaving the conventional catalyst reaction column.

As described later, according to the present invention, the service life of the zeolite catalyst is significantly extended by limiting the amount of such aldehyde compounds flowing into the catalyst bed up to a specific level.

FIG. 1 in the accompanying drawings is a graphical view showing the results of an experimentation carried out to study the influence of formaldehyde on the life of the zeolite catalyst. It depicts the relation of the deactivation constant and activity half-life (the period in which the rate constant of a methanol-consuming reaction decreases to half) of a zeolite catalyst to the amount of formaldehyde inflowing into a reactor. From this figure, it is apparent that there is a sharp increase in the rate of deactivation, when the amount of inflow of formaldehyde exceeds about 0.2 g/hr.kg-cat. It is also noted that where any means was not taken for preventing the reaction system from being contaminated with aldehyde compounds, i.e., the amount of inflow of formaldehyde exceeded about 0.4 g/hr kg-cat., the half-life of reaction activity (the period in which the reaction rate constant k decreases to half, with the proviso that the methanol-consuming reaction is a first order reaction with respect to methanol) was 25% of that obtained with a raw material containing no aldehyde compounds. The half-life was increased to 60% by controlling the amount of inflow to about 0.15 g/hr.kg-cat. Thus, the service life of the zeolite catalyst was increased by twice or more and 4 times or more by controlling the amount of inflow of formaldehyde to 0.15 g/hr.kg-cat., and 0.01 g/hr.kg-cat., respectively.

Thus, according to the present invention, a method for maintaining the activity of a zeolite catalyst in the process for the production of methylamines using a zeolite catalyst as at least one of catalysts applied has been established by controlling the amount of aldehydes esp., formaldehyde compounds, among a number of compounds which may possibly contaminate the reaction system involved, that flow into a catalyst layer to 0.15 g/hr.kg-cat. or lower, preferably 0.1 g/hr.kg-cat. or lower, more preferably 0.05 g/hr.kg-cat. or lower, most preferably 0.01 g/hr.kg-cat. or lower, as calculated in terms of HCHO.

The present invention is applicable to methylamine production processes where a zeolite catalyst is used or an equilibrium-controlled catalyst such as silica-alumina is used in combination with a zeolite catalyst.

The zeolite catalysts used in the present invention should show activity with respect to the synthesis of methylamines, as is the case with Y-type zeolite and mordenite. Especially included in such zeolite catalysts are zeolites exhibiting molecular shape selectivity to the synthesis reaction of methylamines, viz., mordenite, Fu-1, chabasite, erionite, Rho, ZK-1, zeolite A and levynite.

The reaction involved occurs at a lower temperature in comparison with conventional methods, say, 230° to 350° C., preferably 250° to 320° C., and the reaction conditions applied include a pressure of 1 to 50 atm, preferably 5 to 30 atm, an N/C ratio of 1 to 3 (a number ratio of nitrogen atoms to carbon atoms in the reaction system), a space velocity of 600 to 2000/hr and a methanol conversion of 80 to 98%. The removal of aldehyde compounds may rely upon precise and elaborate rectification or chemical treatments by an alkali, sodium bisulfite, etc.

Figure 2:
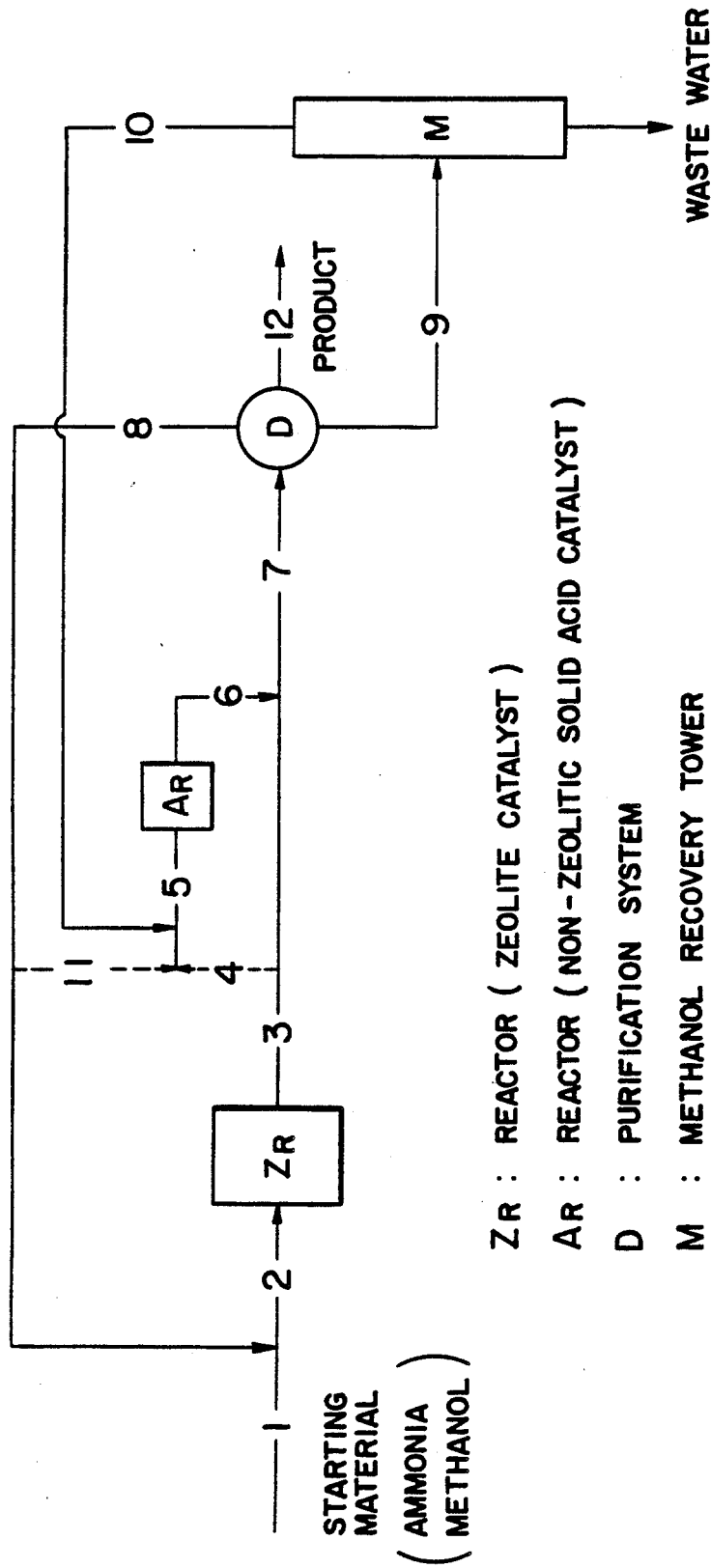
FIG. 2 is a flow-sheet representing a preferable example of the process according to the present invention, wherein an equilibrium-controlled non-zeolitic catalyst is used in combination with a zeolite catalyst.

The process of the present invention may be applied, for example, in the manner as shown in FIG. 2, to a process wherein a zeolite catalyst and a non-zeolitic solid acid catalyst are used in combination.

More particularly, all or a substantial part of the recycled amines from which the product methylamines have been separated in the purification system and unreacted ammonia are fed to a zeolite catalyst reactor ($Z_R$) through line 8 via line 2 together with the starting methanol and ammonia fed through line 1. Substantially all the unreacted methanol (containing aldehyde compounds) recovered in a methanol recovery tower (M) and not subjected to elaborate rectification is fed to a non-zeolitic solid acid catalyst reactor ($A_R$) through line 10 via line 5. To this non-zeolitic solid acid catalyst reactor ($A_R$) are also fed through line 11 the remainder of the recycled amines and unreacted ammonia (which have been fed through line 8) and/or through line 4 part of the product obtained in the zeolite catalyst reactor ($Z_R$), both via line 5.

All or a large portion of the product obtained in the zeolite catalyst reactor ($Z_R$) and all the product obtained in the non-zeolitic solid acid catalyst reactor ($A_R$) are introduced into the purification system (D) respectively through line 3 and line 6, both via line 7. In the purification system (D), the product methylamines are recovered through line 12 while the recycled amines separated therefrom and, unreacted ammonia are transferred in the manner stated above and the unreacted methanol is supplied to the methanol recovery tower (M).

This process requires no elaborate separation of aldehyde compounds in the methanol recovery tower. The aldehyde compounds flowed into the non-zeolitic solid acid catalyst reactor together with the recovered methanol are decomposed therein without affecting the activity and stability of that catalyst in any way.

Examples of non-zeolitic solid acid catalysts for use herein are porous solid acid catalysts predominantly comprising silica and/or alumina such as, γ-alumina and silica-alumina. The reaction conditions to be employed include a temperature of from 350° to 450° C., preferably from 370° to 420° C., and a pressure of from atmospheric pressure to 50 atm, preferably from 5 to 30 atm. If desired, fresh methanol or ammonia may be fed in this reaction.

The reaction conditions required when a zeolite catalyst is used are as mentioned previously.

The present invention will now be explained in more detail with reference to the following examples and comparative examples.

COMPARATIVE EXAMPLE 1

74 ml of Na-H type mordenite (Na content: 0.7 wt %), pellets having a diameter of about 5 mm were packed in a ½B stainless reaction tube having a length of 800 mm together with an inert solid diluent having the same particle diameter, and a mixture of ammonia, methanol, MMA, DMA and TMA ($NH_3$/MMA/DMA/TMA/methanol = 46.0/12.2/0.1/5.0/36.7 wt %), containing 300 ppm or 880 ppm of formaldehyde, was continuously passed therethrough at a reaction temperature of 320° C. and a pressure of 19KSCG to carry out reaction. The effluence was regularly sampled to analyze the amount of unreacted methanol by gas chromatography and measure an activity change with time, which activity is expressed in terms of the rate constant of- the first order reaction with respect to methanol. The results are shown in Table 1(5) and (6).

EXAMPLE 1

Using the same reactor and catalyst as in Comparative Example 1, a similar mixture of ammonia and methanol containing 0-90 ppm of formaldehyde was continuously passed through the reactor under the same conditions to carry out reaction. The results of activity changes with time are shown in Table 1(1)-(4).

COMPARATIVE EXAMPLE 2

Using the same reactor and catalyst as in Comparative Example 1, a similar mixture of ammonia, methanol, MMA, DMA and TMA was passed through the reactor under the same reaction conditions with the addition of or simultaneously with the aliphatic hydrocarbons shown in Table 2(1). The results of activity changes with time are shown in Table 2(1).

COMPARATIVE EXAMPLE 3

Using the same reactor and catalyst as in Comparative Example 1, a similar mixture of ammonia, methanol, MMA, DMA and TMA, containing the aromatic hydrocarbons shown in Table 2(2), was continuously passed through the reactor under the same reaction conditions to carry out reaction. The results of activity changes with time are shown in Table 2(2).

tion system, and the material was then allowed to react at 320° C. over the zeolite catalyst (isothermal reaction) to measure the rate of deactivation. The reaction activity was approximated by the first order reaction with respect to methanol [reaction rate constant k(1/sec)] and the pattern of deactivation by exponential deactivation [k=ko exp(-bt), b: deactivation constant (1/day) and t: the time elapsed (day)]. The service life of the catalyst was expressed in terms of the ratio $\theta/\theta_{HCHO=0}$ of the activity half-life (the period required for k→½k) with respect to the starting material comprising pure ammonia/methanol/methylamine containing no impurities and the rate of $b/b_{HCHO=0}$ of the deactivation constant.

In Example 1, similar experiments were performed with the amount of inflow of formaldehyde smaller than actual case. The figure in this drawing graphically illustrates the results of Comparative Example 1 and Example 1. From this figure, it is apparent that $\theta/\theta_0=0.25$ when the amount of inflow of formaldehyde is about 0.4 g/hr·kg-cat. (the catalyst has a service life of about 2.5 months at this time), and the rate of deactivation sharply increases at a larger amount. When the amount of inflow of formaldehyde is 0.15 g/hr·kg-cat., on the other hand, $\theta/\theta_0$ is about 0.6. In other words, the service life of the catalyst increases by about 2.4 times. This corresponds to a catalyst life of about six months which is almost satisfactory from the industrial point of view. Further, $\theta/\theta_0$ increases to about 0.8 when the amount of inflow of formaldehyde is 0.05 g/hr·kg-cat., and $\theta/\theta_0$ is nearly equal to 1 at 0.01 g/hr·kg-cat., indicating that the catalyst life increases by about 4 times. This corresponds to a catalyst life of as long as about one year or longer which is adequately satisfactory from the industrial point of view.

In Comparative Examples 2 and 3, similar influences

TABLE 1

|  | No. | Formaldehyde (ppm) | Formaldehyde (g/hr · kg — cat) | Reaction Time Elapsed t (day) | Ratio of Reaction Rate Constant k/ko | Deactivation Constant b (1/day) | Ratio of Deactivation Constant $b/b_{HCHO=0}$ | Ratio of Activity Half-Life $\theta/\theta_{HCHO=0}$ |
|---|---|---|---|---|---|---|---|---|
| Ex. 1 | (1) | 0 | 0 | 3.0 | 0.962 | 0.0128 | 1 | 1 |
|  | (2) | 5 | 0.006 | 35.0 | 0.628 | 0.0133 | 1.04 | 0.96 |
|  | (3) | 36 | 0.045 | 5.8 | 0.916 | 0.0157 | 1.18 | 0.85 |
|  | (4) | 90 | 0.11 | 6.0 | 0.887 | 0.0193 | 1.51 | 0.66 |
| Comp. Ex. 1 | (5) | 300 | 0.38 | 19.0 | 0.401 | 0.0482 | 3.77 | 0.27 |
|  | (6) | 880 | 1.10 | 1.1 | 0.396 | 0.826 | 64.5 | 0.015 | ko: Reaction Rate Constant just after the initiation of reaction
k: Reaction Rate Constant after the lapse of t (day) from the initiation of reaction
b: Deactivation Constant k = ko exp (−bt)
$b_{HCHO=0}$: Deactivation Constant when formaldehyde is 0 ppm
θ: Activity Half-Life (t at time of k = ko/2)
$\theta_{HCHO=0}$: Activity Half-Life when formaldehyde is 0 ppm

TABLE 2

|  | No. | Additives Compounds | Additives ppm | Total g/hr · kg — cat | t (day) | k/ko | b (1/day) | b/b₀ | θ/θ₀ |
|---|---|---|---|---|---|---|---|---|---|
| Comp. Ex. 2 | (1) | methane | 470 | 12 | 10 | 0.869 | 0.014 | 1.08 | 0.93 |
|  |  | ethylene | 150 |  |  |  |  |  |  |
|  |  | propylene | 340 |  |  |  |  |  |  |
|  |  | 1-butene | 8600 |  |  |  |  |  |  |
| Comp. Ex. 3 | (2) | toluene | 2000 | 6.3 | 6.5 | 0.915 | 0.014 | 1.08 | 0.93 |
|  |  | xylene | 3000 |  |  |  |  |  |  | b₀: Deactivation Constant in the absence of additives
θ₀: Activity Half-Life in the absence of additives In Comparative Example 1, more than about 0.4 g/hr·kg-cat. of formaldehyde was added to a starting material comprising pure ammonia, methanol and methylamines, in consideration of the case where no means was taken for the removal of impurities from the reaction system, viz., aromatic and aliphatic hydrocarbons. These compounds have no substantial influence upon the catalyst life, even when they are present in an exceedingly large amount as compared with the formaldehyde compounds. It is thus clearly appreciated that only the aldehyde compounds have a specific influence upon the catalyst life even in trace quantities.

COMPARATIVE EXAMPLE 4

About 60 ml of cylindrical Y type zeolite (HY) of about 3 mm in diameter and about 10 mm in length were packed in the reaction tube as used in Comparative Example 1 together with an inert solid diluent of about 5 mm in diameter, and similar starting materials as in Comparative Example 1, now containing 300 ppm or 2000 ppm of formaldehyde, were allowed to react continuously under the same conditions. The results of activity changes with time measured as shown in Table 3(3) and (4).

EXAMPLE 2

Using the same arrangement as in Comparative Example 1 and the same catalyst as in Comparative Example 4, a similar mixture of ammonia, methanol and emthylamines, containing 0 to 90 ppm of formaldehyde, was continuously passed through the arrangement to carry out reaction. The results of activity changes with time measured are shown in Table 3(1) and (2).

What is claimed is:

1. A method for maintaining the activity of a zeolite catalyst in the catalytic production of methylamines methanol and ammonia using a zeolite catalyst as at least one of catalysts applied, which comprises controlling the amount of formaldehyde as impurities flowing into a zeolite catalyst layer to about 0.15 g/hr.kg-cat. or lower.

2. The method according to claim 1, wherein the zeolite catalyst is one which exhibits molecular shape selectivity to the formation of monomethylamine or dimethylamine from methanol and ammonia.

3. The method according to claim 2, wherein the zeolite catalyst is selected from the group consisting of mordenite, Fu-1, chabasite, erionite, Rho, ZK-1, zeolite A and levynite.

4. The method according to claim 1 wherein a non-zeolitic solid acid catalyst is used together with the zeolite catalyst.

5. The method according to claim 1 wherein the amount of aldehyde compounds is controlled to 0.01 g/hr·kg-cat. or lower.

6. The method according to claim 1 wherein the catalytic production of methylamines from methanol and ammonia is carried out under the conditions of a temperature of 230° to 350° C., a pressure of 1 to 50 atm, an N/C ratio (a number ratio of nitrogen atoms to carbon atoms) of 1 to 3, a space velocity of 600 to 2000/hr and a methanol conversion of 80 to 98%.

TABLE 3

| | No. | Formaldehyde (ppm) | Formaldehyde (g/hr · kg — cat) | Reaction Time Elapsed t (day) | Ratio of Reaction Rate Constant k/ko | Deactivation Constant b (1/day) | Ratio of Deactivation Constant $b/b_{HCHO=0}$ | Ratio of Activity Half-Life $\theta/\theta_{HCHO=0}$ |
|---|---|---|---|---|---|---|---|---|
| Ex. 2 | (1) | 0 | 0 | 3 | 0.967 | 0.0112 | 1 | 1 |
| | (2) | 90 | 0.13 | 3 | 0.952 | 0.0164 | 1.46 | 0.68 |
| Comp. Ex. 4 | (3) | 300 | 0.45 | 3 | 0.886 | 0.0404 | 3.61 | 0.28 |
| | (4) | 2000 | 3.0 | 3 | 0.080 | 0.842 | 75.2 | 0.013 | ko: Reaction Rate Constant just after the initiation of reaction
k: Reaction Rate Constant after the lapse of t (day) from the initiation of reaction
b: Deactivation Constant k = ko exp (−bt)
$b_{HCHO=0}$: Deactivation Constant when formaldehyde is 0 ppm
$\theta$: Activity Half-Life (t at time of k = ko/2)
$\theta_{HCHO=0}$: Activity Half-Life when formaldehyde is 0 ppm